United States Patent [19]

Hayashi et al.

[11] Patent Number: 5,534,508
[45] Date of Patent: Jul. 9, 1996

[54] CEPHEM COMPOUNDS AND ANTIMICROBIAL AGENTS

[75] Inventors: Sadao Hayashi, Hirakata; Eiji Nakanishi, Kawasaki; Yasuyuki Kurita, Hirakata; Masahiko Okunishi, Kawasaki, all of Japan

[73] Assignees: Katayama Seiyakusyo Co., Ltd., Osaka; Ajinomoto Co., Inc., Tokyo, both of Japan

[21] Appl. No.: 281,513

[22] Filed: Jul. 28, 1994

[30] Foreign Application Priority Data

Jul. 29, 1993 [JP] Japan ................................. 5-188443

[51] Int. Cl.[6] ...................... C07D 501/46; A61K 31/545
[52] U.S. Cl. ............................................. 514/206; 540/225
[58] Field of Search .......................... 540/225; 514/206, 514/202

[56] References Cited

U.S. PATENT DOCUMENTS

| | | | |
|---|---|---|---|
| 4,751,295 | 6/1988 | Oka et al. | 540/225 |
| 4,833,134 | 5/1989 | Kishimoto et al. | 514/206 |
| 5,336,673 | 8/1994 | Moon et al. | 514/202 |
| 5,373,000 | 12/1994 | Machida et al. | 514/202 |

FOREIGN PATENT DOCUMENTS

| | | |
|---|---|---|
| 0315518 | 5/1989 | European Pat. Off. |
| 0474049 | 3/1992 | European Pat. Off. |
| 3404615 | 8/1984 | Germany. |
| 3512225 | 10/1985 | Germany. |
| 2134522 | 8/1984 | United Kingdom. |
| 2157293 | 10/1985 | United Kingdom. |

OTHER PUBLICATIONS

The Journal of Antibiotics, vol. XLIII, No. 5, pp. 533–534, May 1990, Hajime Kamachi, et al., "SYNTHESIS OF A NEW SERIES OF CEPHALOSPORINS HAVING 3-SUBSTITUTED-AMMONIO-1-PROPENYL GROUP AS THE C-3 SIDE CHAIN".

Patent Abstracts of Japan, JP-A-3-24087, Feb. 1, 1991.

*Primary Examiner*—Nicholas Rizzo
*Attorney, Agent, or Firm*—Oblon, Spivak, McClelland, Maier & Neustadt

[57] ABSTRACT

Herein disclosed are novel cephem compounds represented by the following general formula (I), and novel antimicrobial, and especially anti-MRSA, agents which contain as an active ingredient at least one of the novel cephem compounds and the physiologically acceptable salts thereof.

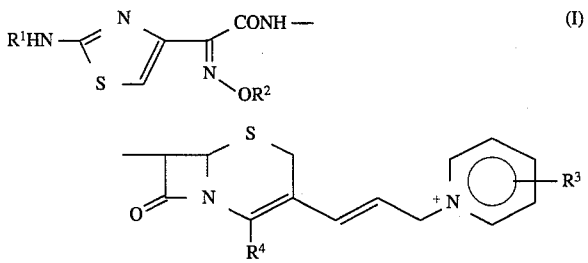

8 Claims, 2 Drawing Sheets

CEPHEM COMPOUNDS AND ANTIMICROBIAL AGENTS

BACKGROUND OF THE INVENTION

1. Field of the Invention

This invention relates to novel cephem compounds whose substituent group at the 3-position is a pyridiniopropenyl group having a substituent group and to antimicrobial agents having anti-MRSA activity which contain at least one of these compounds as an active ingredient. In this connection, MRSA means methicillin-resistant *Staphylococcus aureus*, or a multipledrug resistant *Staphylococcus aureus*.

2. Discussion of the Background

While various antibiotics have been used widely for the treatment of diseases, there have come out some pathogenic bacteria resistant to these antibiotics, such bacteria being called drug resistant bacteria or multipledrug resistant bacteria.

Among these multipledrug resistant bacteria, MRSA is much feared as a possible cause of intractable infection or hospital infection. Several anti-MRSA antibacterial agents have been developed, but request is still strong for the development of more effective novel anti-MRSA antibacterial agents.

SUMMARY OF THE INVENTION

Accordingly, it is an object of the present invention to provide an antibacterial agent, especially one which is effective against MRSA.

The present invention thus provides novel antibacterial agents and novel cephem compounds usable as an active principle of such antibacterial agents, which satisfy the above object and other objects of the present invention which will become apparent from the description of the invention given hereinbelow.

In an aspect of the present invention there are provided some novel cephem compounds. In another aspect of the present invention, there are provided some novel antibacterial agents containing, as an active ingredient, at least one of such cephem compounds.

DETAILED DESCRIPTION OF THE INVENTION

Figure 1:
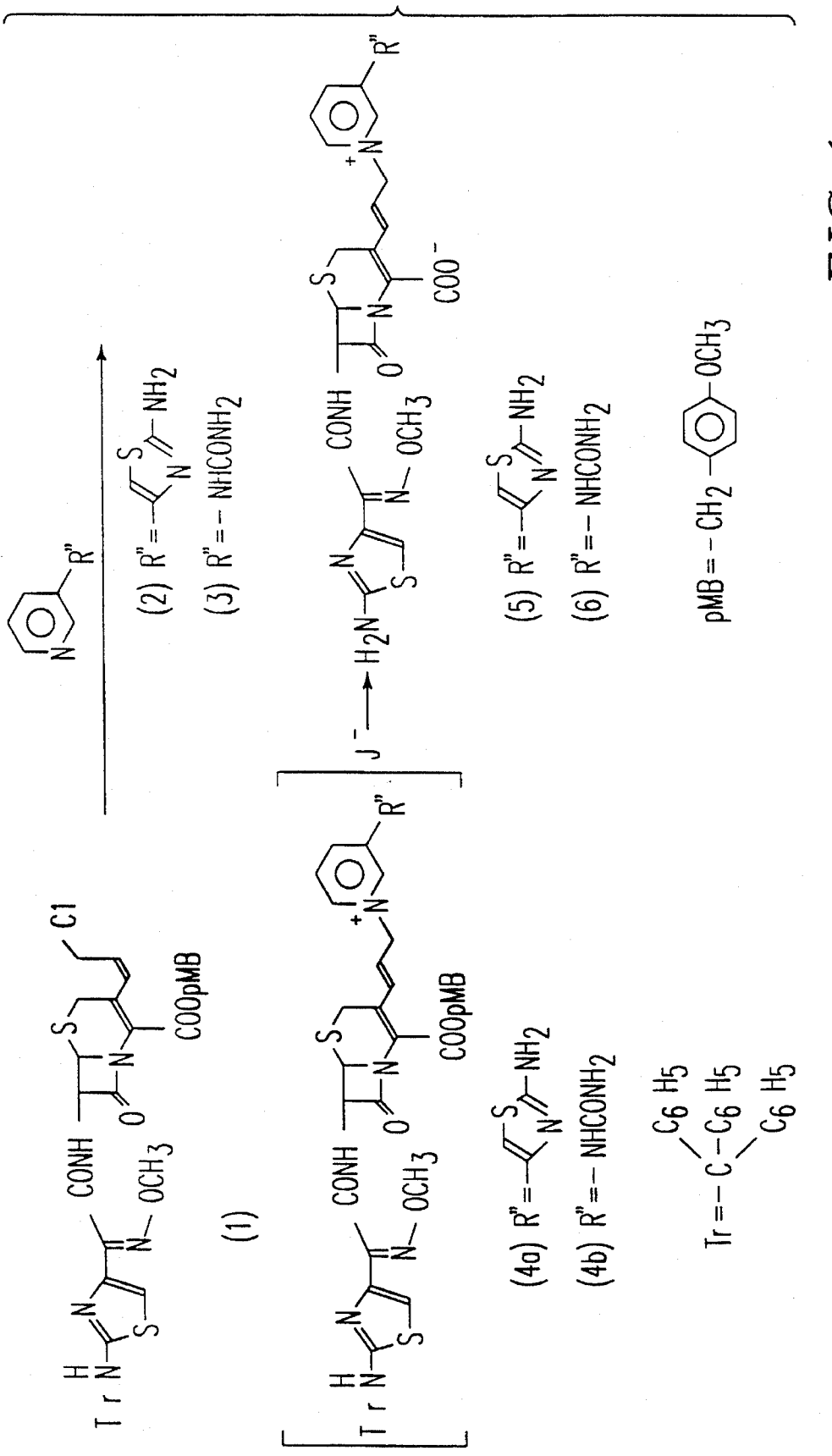
FIG. 1 shows the reaction steps in Examples 1 and 2.

With the aim of attaining the aforementioned objects, the inventors of the present invention have conducted intensive studies to find that the above objects can be attained by certain novel cephem compounds and have succeeded in accomplishing the present invention on the basis of these findings. Accordingly, the present invention relates to novel cephem compounds and antimicrobial agents, especially antibacterial agents effective on MRSA, which contain at least one of the novel cephem compounds as an active ingredient.

The present invention will be described in greater detail, as follows.

A first aspect of the present invention relates to a cephem compound represented by the following general formula (I) and a physiologically acceptable salt thereof.

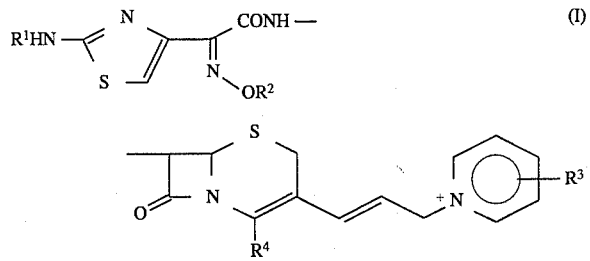

In the above formula, $R^1$ represents a hydrogen atom or a protective group of the amino group; $R^2$ represents a hydrogen atom, a protective group of the hydroxyimino group or an alkyl group; $R^3$ represents an acetyl group, an amino group which may have appropriate substituent groups, a carbamoyl group which may have appropriate substituent groups, a ureido group or a heterocyclic group which may have appropriate substituent groups; and $R^4$ represents a carboxyl or carboxylate group which may be protected. Preferably, $R^3$ is a group represented by the following general formula (1)

wherein $R^5$ represents a hydrogen atom, a methyl group or an amino group.

That is, the compounds of the present invention are novel cephem compounds whose substituent group at the 3-position is a pyridiniopropenyl group having substituent groups.

The compounds of the present invention represented by the general formula (I) can be produced in accordance with methods known per se. That is, a compound represented by the following general formula (Ia) which belongs to the compounds of the present invention can be obtained, e.g., by converting a compound represented by the following general formula (II) into the iodide by its reaction with NaI, allowing the iodide to react with a substituent group-containing pyridine derivative represented by the general formula (III) to obtain the pyridiniopropenyl group-containing compound represented by the following general formula (IV), and then eliminating the protective groups.

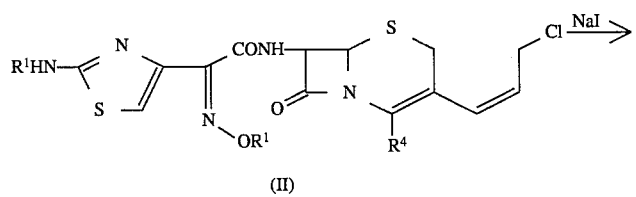

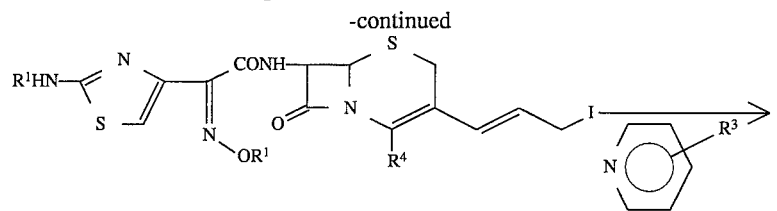

(III)

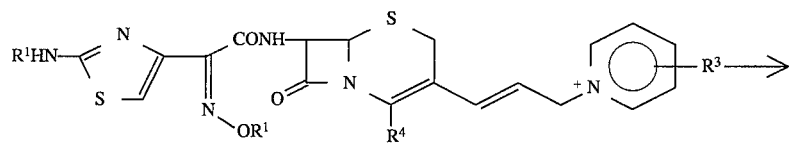

(IV)

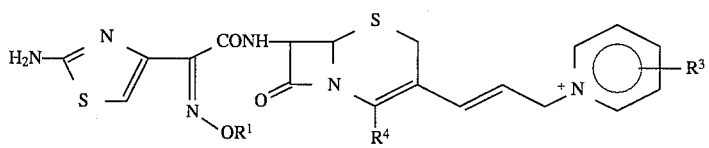

(Ia)

In the above formulae, $R^1$, $R^2$, $R^3$ and $R^4$ are as defined in the foregoing. The protective group of the protected amino group means an easily detachable amino-protecting group usually used in the cephalosporin derivative chemistry, such as formyl, t-butoxycarbonyl, benzyloxycarbonyl, p-nitrobenzyloxycarbonyl, trityl or the like group, which can be eliminated under relatively mild conditions. Examples of the protective groups of the protected hydroxyimino group include formyl, chloroacetyl, benzoyl, p-nitrobenzyl, β,β,β-trichloroethoxycarbonyl, tetrahydropyranyl, trityl and the like groups, which can be eliminated easily under known reaction conditions. The protecting group of the protected carboxyl group means β,β,β-trichloroethyl, p-methoxybenzyl, p-nitrobenzyl, benzhydryl or the like group, which can be eliminated easily.

These compounds may be in the form of salts such as hydrochlorides, nitrates, sulfates, acetates, trifluoroacetates, trichloroacetates, tartarates, p-toluenesulfonates, methanesulfonates and the like.

The compounds of the present invention represented by the general formula (Ia) can also be produced for example by allowing a compound represented by the following general formula (V) to react with a compound represented by the following general formula (VI), and then eliminating the protecting groups as occasion demands.

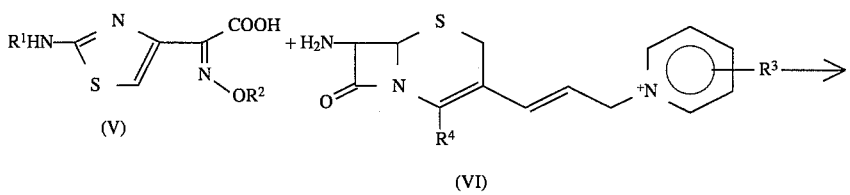

(V)    (VI)

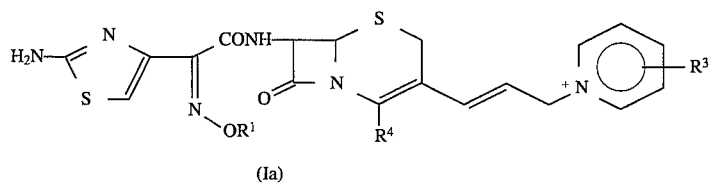

(Ia)

In the above formulae $R^3$, $R^4$, $R^1$ and $R^2$ are as defined in the foregoing.

These compounds may be in the form of salts such as, similar to the aforementioned case, hydrochlorides, nitrates, sulfates, acetates, trifluoroacetates, trichloroacetates, tartarates, p-toluenesulfonates, methanesulfonates and the like.

In the compound represented by the aforementioned general formula (I), the structure of the 2-aminothiazol group moiety is under the equilibrium state of the two tautomers represented by the following equilibrium formula.

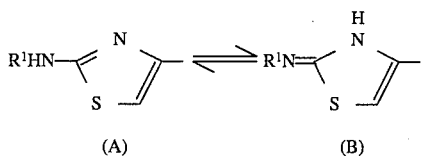

(A)    (B)

Since it is well known that both of the tautomers are present in the equilibrium and mutually changeable state, such isomers can be recognized as substantially the same compound. In consequence, insofar as the present invention is concerned, the aforementioned tautomeric group contained in the aimed-at compounds and starting compounds is shown by the name of one of the tautomers, namely 2-aminothiazol group, and by the above formula (A) for the sake of convenience.

As will be described later in Test Examples, the novel cephem compounds of the present invention have a markedly broad antimicrobial or antibacterial spectrum and show a strong antibacterial activity especially on MRSA. As a matter of course, when these compounds are used as antimicrobial agents in the form of their salts, such salts must be physiologically acceptable.

The novel cephem compounds of the present invention can be used in the form of conventional pharmaceutical preparations by using at least one of them as an active ingredient and mixing it with pharmaceutically acceptable carriers such as organic or inorganic solid or liquid fillers which are suitable for use in peroral, parenteral or external administration. The pharmaceutical preparations may be in the form of either solid preparations such as tablets, granules, powders, capsules and the like or liquid preparations such as solutions, suspensions, syrups, emulsions and the like. As occasion demands, these preparations may contain auxiliaries, stabilizers, moistening agents and other usually used additives. In other words, administration of the inventive preparations can be effected in accordance with the known antimicrobial agent administration methods.

Dose of the novel cephem compounds of the present invention varies depending on its type, age of the patient, type of the disease and the like, but it may be administered in a dose of generally from about 5 to 3,000 mg or higher per adult of about 60 kg in body weight per day. It may be administered in several portions in a day, and, in that case, one portion is about 1 to 1,000 mg.

In this connection, the antimicrobial agent of the present invention did not show acute toxicity when tested.

EXAMPLES

The following Examples and Test Example are provided to further illustrate the present invention.

EXAMPLE 1

Synthesis of Compound 5
(7β-[2-(2-aminothiazol-4-yl)-2-syn-methoxyiminoacetamido]-3-[(E)-3-[3-(2-aminothiazol-4-yl)pyridinio]-1-propenyl]-3-cephem-4-carboxylate)

The reaction in this example is shown in FIG. 1.

(i) Synthesis of Compound 4a.

530 mg of Compound 1 was dissolved in 10 ml of acetone, the resulting solution was added with 291 mg of NaI with stirring under ice cooling, the mixture was stirred at the same temperature for 15 minutes and then at room temperature for 45 minutes followed by distillation removal of the solvent, the resulting residue was extracted in ethyl acetate, the extract was washed with an aqueous sodium chloride solution and dried on $Na_2SO_4$, and then the solvent was distilled off. The thus obtained residue was dissolved in 5 ml of acetonitrile, the resulting solution was added with 109 mg of Compound 2 with stirring under ice cooling, the mixture was stirred at room temperature for 5 hours and 40 minutes followed by distilling off the solvent, the resulting residue was stirred after mixing it with isopropyl alcohol, which was removed thereafter, the resulting residue was solidified by adding ether, and then the thus solidified substance was collected by filtration, washed with ether and dried to obtain 560 mg (80%) of Compound 4a.

Identification data of the Compound 4a are as follows.

IR $v_{max}$ Nujol $cm^{-1}$: 3285, 1778, 1720, 1663, 1612, 1585, 1248, 1221, 1177, 1159, 1101, 1036, 824, 814, 754, 702.

NMR δ ($CDCl_3$+$CD_3OD$) ppm: 3.20, 3.59 (2H, $AB_q$, J=17), 3.70 (3H, s), 4.96 (1H, d, J=4.5), 5.07 (2H, s), 5.21 (2H, m), 5.68 (1H, d, J=4.5), 6.13 (1H, d, J=13), 6.53 (1H, s), 6.67 (1H, s), 6.72 (2H, $AB_q$, J=8.5), 6.8–7.5 (18H, m), 7.6–9.0 (4H, m).

(ii) Synthesis of Compound 5.

A 500 mg portion of the Compound 4a was dissolved in 4 ml of dichloromethane, the resulting solution was added with 0.5 ml of anisole and 2 ml of trifluoroacetic acid with stirring under ice cooling, the mixture was stirred at the same temperature for 15 minutes and then at room temperature for 50 minutes followed by evaporation of the solvent, the resulting residue was again added with 4 ml of trifluoroacetic acid and 1.3 ml of water in this order with stirring under ice cooling, the mixture was stirred at the same temperature for 15 minutes and then at room temperature for 3 hours followed by distilling off the solvent, the resulting residue was solidified by adding isopropyl ether, and then the thus solidified substance was collected by filtration and washed with isopropyl ether to obtain 255 mg of the trifluoroacetate of Compound 5. This was applied to a column packed with 100 ml of polystyrene resin "HP20" manufactured by Mitsubishi Kasei Corp. and developed with water containing 20 to 30% methanol to obtain 29 mg (10%) of Compound 5.

Identification data of the Compound 5 are as follows.

IR $v_{max}$ Nujol $cm^{-1}$: 3322, 3211, 3066, 1778, 1666, 1634, 1312, 1261, 1159, 1111, 1045, 995, 972, 858, 802, 771, 721.

NMR δ (DMSO-$d_6$+$CD_3OD$) ppm: 3.67 (2H, br.s), 3.89 (3H, s), 5.06 (1H, d, J=4.5), 5.33 (2H, d, J=5), 5.66 (1H, d, J=4.5), 6.27 (1H, m), 6.81 (1H, s), 7.02 (1H, m), 7.48 (1H, s), 7.6–9.5 (4H, m).

EXAMPLE 2

Synthesis of Compound 6
(7β-[2-(2-aminothiazol-4-yl)-2-syn-methoxyiminoacetamido]-3-[(E)-3-(3-ureidopyridinio]-1-propenyl]-3-cephem-4-carboxylate)

The reaction in this example is also shown in FIG. 1.

(i) Synthesis of Compound 4b.

Using 880 mg of Compound 1 and 147 mg of Compound 3, the reaction was carried out in the same manner as in the synthesis of Compound 4a to obtain 920 mg (82%) of Compound 4b.

Identification data of the Compound 4b are as follows.

IR $v_{max}$ Nujol $cm^{-1}$: 3375, 3204, 1782, 1715, 1666, 1612, 1585, 1321, 1304, 1248, 1223, 1177, 1157, 1103, 1040, 812, 754, 704.

NMR δ ($CDCl_3$+$CD_3OD$) ppm: 3.92 (3H, s), 4.97 (1H, d, J=4.5), 5.10 (2H, s), 5.23 (2H, m), 5.71 (1H, d, J=4.5), 6.23 (1H, m), 6.53 (1H, s), 6.73 (2H, d, J=8.5), 6.9–7.6 (18H, m), 7.6–8.6 (3H, m), 9.12 (1H, br.s).

(ii) Synthesis of Compound 6.

Using a 900 mg portion of the Compound 4b, the reaction was carried out in the same manner as in the synthesis of Compound 5 to obtain 131 mg (26%) of Compound 6.

Identification data of the Compound 6 are as follows.

IR $v_{max}$ Nujol cm$^{-1}$: 3339, 3196, 3088, 1771, 1693, 1681, 1634, 1290, 1204, 1155, 1115, 1045, 997, 972, 887, 858, 806, 723, 679.

NMR δ (DMSO-d$_6$+CD$_3$OD) ppm: 3.68 (2H, br.s), 3.92 (3H, s), 5.15 (1H, d, J=4.5), 5.30 (2H, br.d, J=6), 5.70 (1H, d, J=4.5), 6.32 (1H, m), 6.85 (1H, s), 6.99 (1H, br.d, J=13), 7.65–8.70 (3H, m), 9.11 (1H, br.s).

EXAMPLE 3

Synthesis of Compound 12 (7β-[2-(2-aminothiazol-4-yl)-2-syn-hydroxyiminoacetamido]-3-[(E)-3-[3-(2-aminothiazol-4-yl)pyridinio]-1-propenyl]-3-cephem-4-carboxylate).

Figure 2:
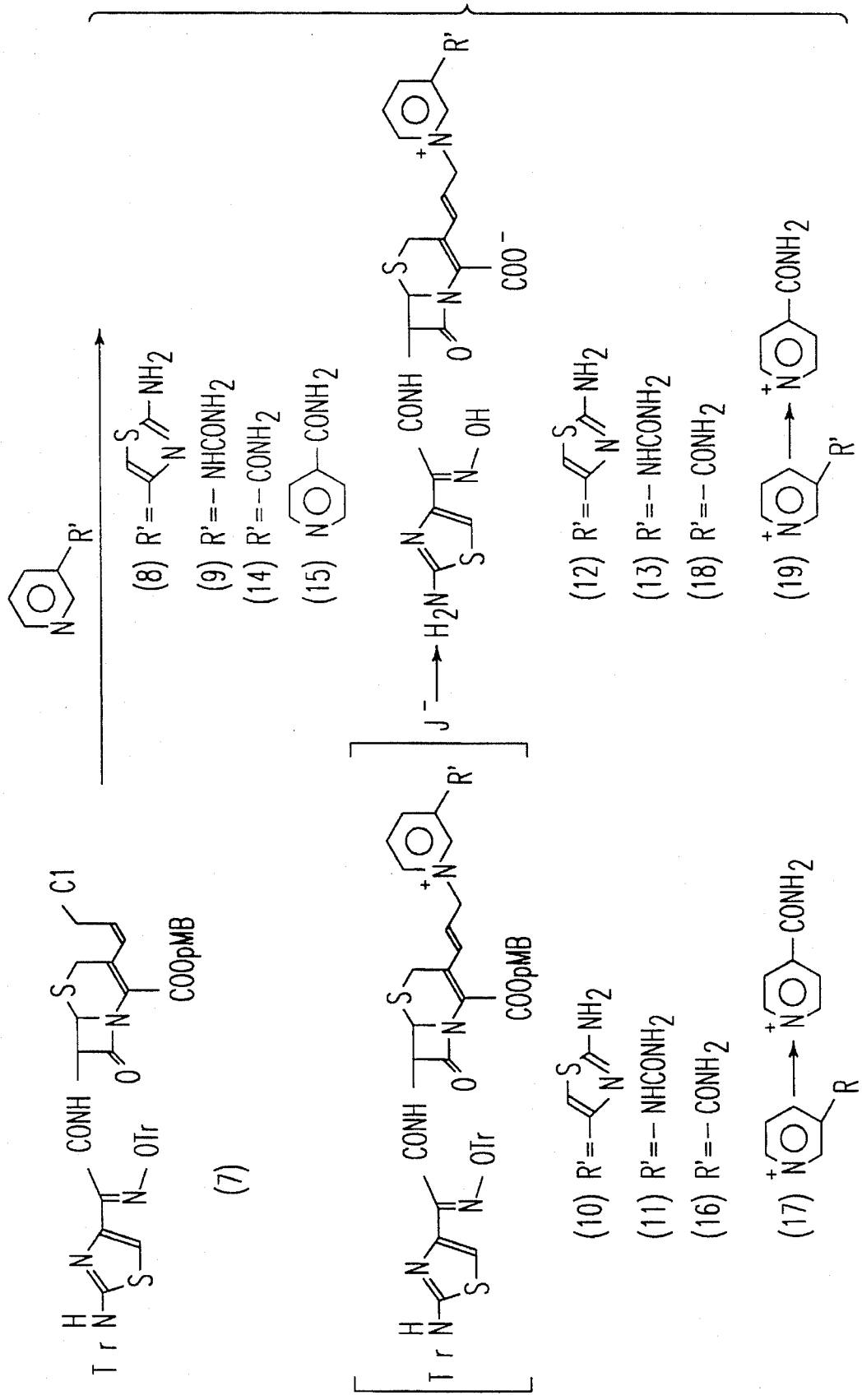
FIG. 2 shows the reaction steps in Examples 3 to 6.

The reaction in this example is shown in FIG. 2.

(i) Synthesis of Compound 10 (p-methoxybenzyl 7β-[2-(2-tritylaminothiazol-4-yl)-2 -syn-trityloxyiminoacetamido] -3-[(E)-3-[3-(2-aminothiazol-4-yl)pyridinio]-1-propenyl]-3-cephem-4-carboxylate iodide).

917 mg of Compound 7 (p-methoxybenzyl 7β-[2-(2-tritylaminothiazol-4-yl)-2 -syn-trityloxyiminoacetamido]-3-[(Z)-3-chloro-1-propenyl]-3-cephem-4-carboxylate) was dissolved in 25 ml of acetone, the resulting solution was added with 394 mg of NaI with stirring under ice cooling, the mixture was stirred at the same temperature for 10 minutes and then at room temperature for 45 minutes followed by distillation removal of the solvent, the resulting residue was dissolved in ethyl acetate, and the solution was washed with an aqueous sodium chloride solution and dried on Na$_2$SO$_4$ followed by removing the solvent by evaporation. The thus obtained residue was added with 140 mg of Compound 8 (3-(2-aminothiazol-4-yl)pyridine) and made into a solution by adding 10 ml of DMF under ice cooling, the thus obtained solution was stirred at room temperature for 4 hours followed by distilling off the DMF under reduced pressure, the resulting residue was solidified by adding isopropyl ether, and then the thus solidified substance was collected by filtration and washed with isopropyl ether to obtain 854 mg (74%) of Compound 10.

Identification data of the Compound 10 are as follows.

IR $v_{max}$ Nujol cm$^{-1}$: 3287, 1784, 1722, 1666, 1612, 1304, 1250, 1221, 1177, 1157, 1101, 1061, 1032, 1003, 966, 827, 754, 700, 660.

NMR δ (CDCl$_3$+CD$_3$OD) ppm: 3.28, 3.56 (2H, AB$_q$, J=18), 3.71 (3H, s), 5.03 (1H, d, J=4.5), 5.14 (2H, s), 5.2–5.5 (2H, m), 6.42 (1H, s), 6.77 (2H, d, J=9), 6.8–7.8 (33H, m), 7.9–9.4 (4H, m).

(ii) Synthesis of Compound 12.

854 mg of Compound 10 was dissolved in 3 ml of dichloromethane, the resulting solution was added dropwise with 0.6 ml of anisole and 1.5 ml of trifluoroacetic acid in this order with stirring under ice cooling, the resulting mixture was stirred at the same temperature for 10 minutes and then at room temperature for 1 hour followed by evaporation of the solvent, the thus obtained residue was again added dropwise with 3.0 ml of trifluoroacetic acid and 1.0 ml of water in this order with stirring under ice cooling, the resulting mixture was stirred at the same temperature for 10 minutes and then at room temperature for 3 hours followed by distilling off the solvent under reduced pressure, the thus obtained residue was solidified by adding isopropyl ether, and then the thus solidified substance was collected by filtration and washed with isopropyl ether to obtain 413 mg of the trifluoroacetate of Compound 12. This was applied to a column packed with 100 ml of "HP20" and developed with water and then with 20% methanol in water to obtain 70 mg (13%) of Compound 12.

Identification data of the Compound 12 are as follows.

IR $v_{max}$ Nujol cm$^{-1}$: 3267, 3169 (sh), 3061, 1774, 1666 (sh), 1632, 1582, 1545, 1508, 1310, 1259, 1157, 1111, 1059, 1011, 972, 856, 810, 721, 675.

NMR δ (DMSO-d$_6$+CD$_3$OD) ppm: 3.54, 3.87 (2H, AB$_q$, J=18), 5.14 (1H, d, J=4.5), 5.46 (2H, m), 5.71 (1H, d, J=4.5), 6.37 (1H, m), 6.78 (1H, s), 6.98 (1H, d, J=15), 7.47 (1H, s), 7.98 (1H, m), 8.73 (2H, m), 9.26 (1H, br.s).

EXAMPLE 4

Synthesis of Compound 13 (7β-[2-(2-aminothiazol-4-yl)-2-syn-hydroxyiminoacetamido]-3-[(E)-3-(3-ureidopyridinio) -1-propenyl]-3-cephem-4-carboxylate)

The reaction in this example is also shown in FIG. 2.

(i) Synthesis of Compound 11 (p-methoxybenzyl 7β-[2-(2-tritylaminothiazol-4-yl)-2 -syn-trityloxyiminoacetamido] -3-[(E)-3-(3-ureidopyridinio)-1-propenyl]-3-cephem-4-carboxylate iodide).

Using 912 mg of Compound 7 and 111 mg of Compound 9 (3-ureidopyridine), the reaction was carried out in the same manner as in the synthesis of Compound 10 to obtain 876 mg (76%) of Compound 11.

Identification data of the Compound 11 are as follows.

IR $v_{max}$ Nujol cm$^{-1}$: 3362, 3190, 1787, 1687, 1657, 1302, 1248, 1221, 1175, 1157, 1101, 1032, 1003, 966, 827, 752, 700.

NMR δ (CDCl$_3$+CD$_3$OD) ppm: 3.23, 3.49 (2H, AB$_q$, J=18), 3.72, 4.97 (1H, d, J=4.5), 5.06 (2H, s), 5.13 (2H, s), 5.76 (1H, m), 5.84 (1H, d, J=4.5), 6.40 (1H, s), 6.76 (2H, d, J=8.5), 6.5–7.6 (33H, m), 7.7–9.2 (4H, m).

(ii) Synthesis of Compound 13.

Using 876 mg of Compound 11, the reaction was carried out in the same manner as in the synthesis of Compound 12 to obtain 79 mg (16%) of Compound 13.

Identification data of the Compound 13 are as follows.

IR $v_{max}$ Nujol cm$^{-1}$: 3308, 3192, 3092, 1771, 1692, 1634, 1556, 1290, 1196, 1155, 1115, 1055, 1009, 972, 808, 679.

NMR δ (DMSO-d$_6$+CD$_3$OD) ppm: 3.70 (2H, br.s), 5.16 (1H, d, J=4.5), 5.28 (2H, m), 5.75 (1H, d, J=4.5), 6.37 (1H, m), 6.83 (1H, s), 7.00 (1H, d, J=14), 7.83 (1H, d.d, J=6, 8), 8.25 (1H, d, J=8), 8.45 (1H, d, J=6), 9.13 (4H, br.s).

EXAMPLE 5

Synthesis of Compound 18 (7β-[2-(2-aminothiazol-4-yl)-2-syn-hydroxyiminoacetamido]-3-[(E)-3-(3-carbamoylpyridinio)-1-propenyl]-3-cephem-4-carboxylate)

The reaction in this example is also shown in FIG. 2.

(i) Synthesis of Compound 16 (p-methoxybenzyl 7β-[2-(2-tritylaminothiazol-4-yl)-2 -syn-trityloxyiminoacetamido] -3-[(E)-3-(3-carbamoylpyridinio)-1-propenyl]-3-cephem-4-carboxylate iodide).

Using 1.035 g of Compound 7 and 127 mg of Compound 14 (nicotinamide), the reaction was carried out in the same manner as in the synthesis of Compound 10 to obtain 1.02 g (82%) of Compound 16.

Identification data of the Compound 16 are as follows.

NMR δ (CDCl$_3$+CD$_3$OD) ppm: 3.23, 3.50 (2H, AB$_q$), 3.68 (3H, s), 4.94 (1H, d, J=4.5), 5.12 (2H, s), 5.30 (2H, m), 5.78 (1H, d, J=4.5), 5.92 (1H, m), 6.32 (1H, s), 6.70 (2H, d, J=8.5), 6.5–7.5 (33H, m), 7.7–9.1 (4H, m).

IR ν$_{max}$ Nujol cm$^{-1}$: 3325, 3188, 1784, 1722, 1666, 1612, 1247, 1221, 1177, 1157, 1103, 1032, 1003, 966, 827, 752, 700.

(ii) Synthesis of Compound 18.

Using a 930 mg portion of the Compound 16, the reaction was carried out in the same manner as in the synthesis of Compound 12 to obtain 37 mg (9.5%) of Compound 18.

Identification data of the Compound 18 are as follows.

NMR δ (DMSO-d$_6$+CD$_3$OD) ppm: 3.66 (2H, br.s), 5.14 (1H, d, J=4.5), 5.40 (2H, m), 5.73 (1H, d, J=4.5), 6.25 (1H, m), 6.68 (1H, s), 7.02 (1H, d, J=15), 8.0–9.2 (3H, m), 9.36 (4H, br.s).

IR ν$_{max}$ Nujol cm$^{-1}$: 3327, 3182, 3094, 1770, 1681, 1634, 1589, 1556, 1188, 1140, 1117, 1059, 1009, 970, 810, 756, 733, 679.

EXAMPLE 6

Synthesis of Compound 19 (7β-[2-(2-aminothiazol-4-yl)-2-syn-hydroxyiminoacetamido]-3-[(E)-3-(4-carbamoylpyridinio)-1-propenyl]-3-cephem-4-carboxylate)

The reaction in this example is also shown in FIG. 2.

(i) Synthesis of Compound 17 (p-methoxybenzyl 7β-[2-(2-tritylaminothiazol-4-yl)-2-syn-trityloxyiminoacetamido]-3-[(E)-3-(4-carbamoylpyridinio)-1-propenyl]-3-cephem-4-carboxylate iodide).

Using 1.22 g of Compound 7 and 142 mg of Compound 15 (isonicotinamide), the reaction was carried out in the same manner as in the synthesis of Compound 10 to obtain 1.24 g (84%) of Compound 17.

Identification data of the Compound 17 are as follows.

NMR δ (CDCl$_3$+CD$_3$OD) ppm: 3.23, 3.51 (2H, AB$_q$), 3.66 (3H, s), 4.97 (1H, d, J=4.5), 5.11 (2H, s), 5.20 (2H, m), 5.72 (1H, d, J=4.5), 6.43 (1H, s), 6.78 (2H, d, J=8.5), 6.5–7.6 (33H, m), 7.58, 8.49 (4H, AB$_q$, J=5).

IR ν$_{max}$ Nujol cm$^{-1}$: 3325, 3188, 1784, 1720, 1666, 1612, 1250, 1219, 1175, 1159, 1101, 1034, 1003, 966, 922, 827, 754, 700.

(ii) Synthesis of Compound 19.

Using a 1.13 g portion of the Compound 17, the reaction was carried out in the same manner as in the synthesis of Compound 12 to obtain 34 mg (7%) of Compound 19.

Identification data of the Compound 19 are as follows.

NMR δ (DMSO-d$_6$+CD$_3$OD) ppm: 3.67 (2H, br.s), 5.24 (1H, d, J=4.5), 5.43 (2H, m), 5.73 (1H, d, J=4.5), 6.5 (1H, m), 6.73 (1H, s), 6.94 (1H, d, J=16), 8.33, 9.07 (4H, AB$_q$, J=16).

IR ν$_{max}$ Nujol cm$^{-1}$: 3308, 3167, 3121, 3057, 1771, 1682, 1634, 1568, 1169, 1055, 1009, 968, 864, 808, 770, 721.

TEST EXAMPLE 1

Test on Antibacterial Potency Against Standard Strains

The minimum growth inhibitory concentration (MIC, μg/ml) of the compounds for each of the 25 standard laboratory strains (standard strains) shown in Table 1 was determined in accordance with the standard method of the Japan Chemotherapical Society (*Chemotherapy*, 29, 76–79 (1981) under "Re-revision of the measuring methods of minimum growth inhibitory concentration (MIC)").

That is, by using each test strain cultured overnight at 37° C. in a Muller-Hinton broth, there was prepared a bacterial solution with a cell density of 1×10$^6$ CFU/ml in the same broth. The bacterial solution was inoculated into the Muller-Hinton agar media each containing respectively one test agent (i.e., compound) and, after overnight incubation at 37° C., the minimum concentration that inhibited growth of the bacteria was determined and expressed as MIC. The results are shown in Table 1.

*Staphylococcus aureus* 167 and *Staphylococcus aureus* 195 used in the test were MRSA. CTM (cefotiam) and FMOX (flomoxef) were used as the control agents.

TABLE 1

| | Antibacterial potency against standard strains | | | | | | | |
| --- | --- | --- | --- | --- | --- | --- | --- | --- |
| | Drugs tested | | | | | | | |
| Strains tested | Compd. 5 | Compd. 6 | Compd. 12 | Compd. 13 | Compd. 18 | Compd. 19 | FMOX | CTM |
| S. aureus 209p JC-1 | 0.39 | 0.39 | 0.1 | 0.1 | 0.1 | 0.1 | 0.39 | 0.78 |
| S. aureus Smith | 0.39 | 0.39 | 0.1 | 0.2 | 0.1 | 0.2 | 0.39 | 0.78 |
| S. aureus 167 | 100 | 50 | 25 | 12.5 | 50 | 100 | 150 | >100 |
| S. aureus 195 | 12.5 | 12.5 | 1.56 | 1.56 | 3.13 | 3.13 | 3.13 | >100 |
| S. epidemidis IAM 1296 | 0.2 | 0.2 | 0.05 | 0.025 | 0.05 | 0.05 | 0.2 | 0.39 |
| M. luteus ATCC 9341 | 0.025 | 0.025 | 0.05 | 0.05 | 0.05 | 0.05 | 0.1 | 0.39 |
| B. subtilis ATCC 6633 | 0.39 | 0.2 | 0.2 | 0.2 | 0.1 | 0.2 | 0.2 | 0.39 |
| E. coli JC-2 | 0.025 | 0.025 | 0.05 | 0.025 | 0.05 | 0.1 | 0.1 | 0.2 |
| E. coli CSH2(RK1) | 0.05 | 0.025 | 0.2 | 0.05 | 0.1 | 0.2 | 0.1 | 0.2 |
| E. coli CSH2(RE45) | 0.2 | 0.1 | 0.1 | 0.05 | 0.05 | 0.1 | 0.1 | 0.39 |
| K. pneuminiae IFO 3317 | 0.025 | 0.025 | 0.05 | 0.025 | 0.05 | 0.05 | 0.05 | 0.2 |
| K. pneuminiae No. 42 | 0.2 | 0.1 | 0.1 | 0.05 | 0.1 | 0.1 | 0.1 | 0.39 |
| P. mirabilis IFO 3849 | 0.1 | 0.025 | 0.1 | 0.05 | 0.1 | 0.2 | 0.2 | 0.39 |
| P. vulugaris OX-19 | 0.025 | 0.025 | 0.05 | 0.05 | 0.1 | 0.1 | 0.39 | 0.39 |
| M. morganii IFO 3848 | 0.025 | 0.025 | 0.025 | 0.025 | 0.05 | 0.05 | 0.39 | 0.2 |
| S. marcescens IAM 1184 | 0.025 | 0.025 | 0.1 | 0.05 | 0.05 | 0.1 | 0.2 | 3.13 |
| S. marcescens No. 16-2 | 1.56 | 0.78 | 12.5 | 6.25 | 12.5 | 12.5 | 100 | >100 |

TABLE 1-continued

Antibacterial potency against standard strains

| | Drugs tested | | | | | | | |
|---|---|---|---|---|---|---|---|---|
| Strains tested | Compd. 5 | Compd. 6 | Compd. 12 | Compd. 13 | Compd. 18 | Compd. 19 | FMOX | CTM |
| E. cloacae ATCC 13407 | 0.2 | 0.2 | 0.39 | 0.1 | 0.1 | 0.39 | 100 | >100 |
| E. cloacae Nek39 | 3.13 | 3.13 | 6.25 | 6.25 | 6.25 | 12.5 | 100 | >100 |
| C. freundii ATCC 8090 | 0.025 | 0.025 | 0.05 | 0.025 | 0.05 | 0.05 | 0.2 | 0.78 |
| P. aeruginosa NCTC 10490 | 1.56 | 0.39 | 3.13 | 1.56 | 1.56 | 1.56 | >100 | 100 |
| P. aeruginosa AKR17 | >100 | >100 | >100 | >100 | >100 | >100 | >100 | >100 |
| P. cepacia CN 9113 | 50 | 50 | >100 | >100 | >100 | >100 | 100 | >100 |
| A. faecalis ATCC 3750 | 0.78 | 0.39 | 1.56 | 0.78 | 0.78 | 1.56 | 0.1 | 3.13 |
| A. calcoaceticos T59 | 12.5 | 6.25 | 12.5 | 3.13 | 3.13 | 3.13 | 100 | >100 |

It can be understood from Table 1 that the novel cephem compounds of the present invention show a strong wide-ranging antibacterial spectrum.

TEST EXAMPLE 2

Test on Antibacterial Potency Against Clinically Isolated MRSA

A test on the antibacterial potency against clinically isolated MRSA was conducted in the following way.

That is, using 47 strains of clinically isolated MRSA, MIC was determined for each of the test strains in accordance with the standard method of the Japan Chemotherapical Society as in Test Example 1, and the minimum growth inhibitory concentration which inhibited growth of 50% of the strains tested was expressed as $MIC_{50}$ (µg/ml), and the minimum growth inhibitory concentration which inhibited growth of 90% of the strains tested was expressed as $MIC_{90}$ (µg/ml).

In this test, FMOX was used as the control agent.

The results are shown in Table 2.

TABLE 2

Antibacterial potency against clinically isolated MRSA

| | Antimicrobial potency | |
|---|---|---|
| Drugs tested | $MIC_{50}$ (µg/ml) | $MIC_{90}$ (µg/ml) |
| Compound 6 | 13.8 | 67.0 |
| Compound 13 | 0.83 | 5.08 |
| Compound 18 | 2.63 | 22.2 |
| Compound 19 | 2.92 | 17.37 |
| FMOX | 5.13 | 32.09 |

EFFECTS OF THE INVENTIONS

Novel antimicrobial agents, especially those having excellent antibacterial potency against MRSA, are provided by the present invention.

What is claimed is:

1. A cephem compound having the formula (I):

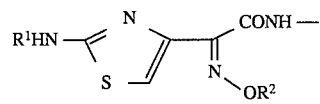

-continued

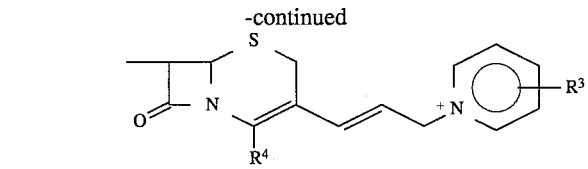

wherein $R^1$ is hydrogen;

$R^2$ is hydrogen;

$R^4$ is a carboxyl or carboxylate group which may be protected;

$R^3$ is selected from the group consisting of ureido and a group having the formula (1),

wherein $R^5$ is amino; and physiologically acceptable salts thereof.

2. The cephem compound of claim 1, wherein $R^3$ is ureido.

3. The cephem compound of claim 1, wherein $R^3$ is a group having formula (1).

4. The cephem compound of claim 1, wherein said compound is selected from the group consisting of:

(7β-[2-(2-aminothiazol-4-yl)-2-syn-hydroxyiminoacetamido]-3-[(E)-3-[3-(2 -aminothiazol-4-yl)pyridinio]-1-propenyl]-3-cephem-4-carboxylate); and (7β-[2-(2-aminothiazol-4-yl)-2-syn-hydroxyiminoacetamido]-3-[(E)-3-(3 -ureidopyridinio)-1-propenyl]-3-cephem-4-carboxylate).

5. An antimicrobial composition, comprising the cephem compound of claim 1 or a physiologically acceptable salt thereof, and a physiologically acceptable carrier.

6. An antimicrobial composition, comprising the cephem compound of claim 4 or a physiologically acceptable salt thereof, and a physiologically acceptable carrier.

7. The cephem compound of claim 1, wherein said compound is 7β-[2-(2-aminothiazole-4-yl)-2-syn-hydroxyiminoacetamido]-3-[(E)-3-[3-(2 -aminothiazole-4-yl)pyridinio]-1-propenyl]-3-cephem-4-carboxylate.

8. The cephem compound of claim 1, wherein said compound is 7β-[2-(2-aminothiazole-4-yl)-2-syn-hydroxyiminoacetamido]-3-[(E)-3-[3 -ureidopyridinio)-1-propenyl]-3-cephem-4-carboxylate.

* * * * *